US010292854B2

(12) United States Patent
Abu Dayyeh

(10) Patent No.: US 10,292,854 B2
(45) Date of Patent: May 21, 2019

(54) GASTROINTESTINAL TRACT BYPASS DEVICES

(71) Applicant: Mayo Foundation for Medical Education and Research, Rochester, MN (US)

(72) Inventor: Barham K. Abu Dayyeh, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 186 days.

(21) Appl. No.: 15/303,333

(22) PCT Filed: Apr. 10, 2015

(86) PCT No.: PCT/US2015/025370
§ 371 (c)(1),
(2) Date: Oct. 11, 2016

(87) PCT Pub. No.: WO2015/160662
PCT Pub. Date: Oct. 22, 2015

(65) Prior Publication Data
US 2017/0027729 A1    Feb. 2, 2017

Related U.S. Application Data

(60) Provisional application No. 61/979,203, filed on Apr. 14, 2014.

(51) Int. Cl.
*A61F 5/00* (2006.01)
*A61B 17/11* (2006.01)
*A61B 17/22* (2006.01)

(52) U.S. Cl.
CPC ........ *A61F 5/0076* (2013.01); *A61B 17/1114* (2013.01); *A61F 5/0036* (2013.01); *A61F 5/0089* (2013.01); *A61B 2017/22069* (2013.01)

(58) Field of Classification Search
CPC .... A61F 5/0076; A61F 5/0036; A61F 5/0089; A61B 17/1114; A61B 2017/22069
See application file for complete search history.

(56) References Cited

U.S. PATENT DOCUMENTS 8,012,140 B1    9/2011  Kagan et al.
2002/0143387 A1* 10/2002 Soetikno ............... A61F 2/95
                                                                623/1.15

(Continued)

OTHER PUBLICATIONS

International Preliminary Report on Patentability in International Application No. PCT/US2015/025370, dated Oct. 27, 2016, 7 pages.

(Continued)

*Primary Examiner* — Philip R Wiest
(74) *Attorney, Agent, or Firm* — Fish & Richardson P.C.

(57) ABSTRACT

Devices and methods can be used for the endoscopic treatment of conditions such as obesity and metabolic diseases. For example, this document provides devices and methods for bypassing portions of the gastrointestinal tract to reduce nutritional uptake. The devices provided herein can be endoscopically implanted such that direct visualization of the entire implant location within the gastrointestinal tract is attained. In some embodiments, the device is distally deployed utilizing a technique that is like that of single or double-balloon enteroscopy.

15 Claims, 4 Drawing Sheets

(56) References Cited

U.S. PATENT DOCUMENTS

| | | | |
|---|---|---|---|
| 2004/0039452 A1* | 2/2004 | Bessler | A61F 2/07 |
| | | | 623/23.65 |
| 2011/0245752 A1 | 10/2011 | Levine et al. | |
| 2011/0251555 A1 | 10/2011 | Ducharme et al. | |
| 2011/0257580 A1 | 10/2011 | Meade et al. | |
| 2013/0079603 A1* | 3/2013 | Vargas | A61F 2/04 |
| | | | 600/309 |

OTHER PUBLICATIONS

International Search Report in International Application No. PCT/US2015/025370, dated Jul. 15, 2015, 15 pages.
Tierney et al., "Overtube use in gastrointestinal endoscopy," *Gastrointestinal Endoscopy.*, 70(5):828-834, 2009.

* cited by examiner

GASTROINTESTINAL TRACT BYPASS DEVICES

CROSS REFERENCE TO RELATED APPLICATIONS

This application is a National Stage application under 35 U.S.C. § 371 of International Application No. PCT/US2015/025370, having an International Filing Date of Apr. 10, 2015, which claims the benefit of U.S. Provisional Ser. No. 61/979,203 filed Apr. 14, 2014. This disclosure of the prior application is considered part of (and is incorporated by reference in) the disclosure of this application.

BACKGROUND

1. Technical Field

This document relates to devices and methods for the medical treatment of conditions such as obesity and metabolic diseases. For example, this document relates to devices and methods for bypassing portions of the gastrointestinal tract to reduce weight and/or to improve diabetes control.

2. Background Information

Obesity is a global problem crossing age, ethnic, and socioeconomic boundaries. In general, obesity means having too much body fat. Morbid obesity is a serious health condition that can interfere with basic physical functions such as breathing or walking. Individuals who are morbidly obese are at greater risk for illnesses including diabetes, high blood pressure, sleep apnea, gastroesophageal reflux disease, infertility, low back pain, asthma, gallstones, osteoarthritis, heart disease, and cancer. Billions of dollars are spent each year treating millions of individuals around the world suffering from such diseases. Many people suffering from morbid obesity find it nearly impossible to lose weight by controlling their diet and exercising.

Roux-en-Y gastric bypass (RYGB) is a bariatric surgical procedure that exerts its effects by bypassing the majority of the stomach and proximal small intestines; thus, excluding them from contact with nutrients. Both gastric and small intestinal components of RYGB can be useful for induction of weight loss and/or ameliorating metabolic diseases such as diabetes.

SUMMARY

This document provides devices and methods for the endoscopic treatment of conditions such as obesity and metabolic diseases. For example, this document provides devices and methods for bypassing portions of the gastrointestinal (GI) tract which can result in decreased nutritional uptake, weight loss, and improvement in diabetes control. The devices provided herein can be endoscopically implanted over a balloon-assisted enteroscope or over a colonoscope; such that direct visualization of the device's entire implant path and deep positioning within the small intestines can be attained in some iterations of the device. In some embodiments, the devices are distally deployed and guided to a target position endoscopically under direct endoscopic visualization.

In one implementation, a method for reducing weight and caloric uptake of a mammal comprises: inserting a sleeve device deployment system into a GI tract of the mammal; visualizing, using the endoscope, a portion of the GI tract in which the sleeve device will be deployed, including visualizing the portion of the GI tract in which the distal stent will be deployed; deploying the sleeve device such that each of the proximal and distal stents are reconfigured to have a diametrical profile that is larger than the low profile delivery configuration of each of the proximal and distal stents, and such that each of the proximal and distal stents make contact with surrounding tissue of the GI tract so as to fixate each of the proximal and distal stents in relation to the surrounding tissue of the GI tract; and withdrawing the endoscope and the over-tube while leaving the sleeve device within the GI tract. The sleeve device deployment system comprises: an endoscope; an over-tube including a lumen in which at least a portion of the endoscope is disposed; and a sleeve device comprising a proximal stent, a distal stent, and a tube extending between the proximal stent and the distal stent and attached to each of the proximal and distal stents. Wherein the tube and each of the proximal and distal stents are disposed on the over-tube, and wherein each of the proximal and distal stents are configured in a low profile delivery configuration during the inserting.

Such a method for reducing weight and caloric uptake of a mammal may optionally include one or more of the following features. The mammal may be a human. The method may further comprise, prior to the withdrawing, injecting a fluid into a space between the over-tube and the sleeve device. The deploying may further comprise reconfiguration of the distal stent to have the diametrical profile that is larger than the low profile delivery configuration prior to reconfiguration of the proximal stent to have the diametrical profile that is larger than the low profile delivery configuration. The sleeve device deployment system may be steerable, and the inserting may include steering the sleeve device deployment system within the GI tract. The proximal stent may be deployed so as to make contact with surrounding tissue of the GI tract in a pyloric region of the GI tract. The proximal stent may be deployed so as to make contact with surrounding tissue of the GI tract near an esophageal sphincter of the GI tract. The sleeve device may further comprise one or more radiopaque markers, and fluoroscopy may be used to visualize a location of at least a portion of the sleeve device prior to the deploying.

In another implementation, a sleeve device deployment system that is configured to deploy a sleeve device into a GI tract of a mammal comprises: an endoscope; an over-tube including a lumen in which at least a portion of the endoscope is disposed; and a sleeve device comprising a proximal stent, a distal stent, and a tube extending between the proximal stent and the distal stent and attached to each of the proximal and distal stents. The tube and each of the proximal and distal stents are configured to be disposed on the over-tube for deployment of the sleeve device and separated from the over-tube so as to deploy the sleeve device, and each of the proximal and distal stents are configurable in a low profile delivery configuration and a deployed configuration that has a diametrical profile that is larger than the low profile delivery configuration.

Such a sleeve device deployment system may optionally include one or more of the following features. The sleeve device deployment system may be configured to deploy the sleeve device by reconfiguring the distal stent prior to reconfiguring the proximal stent. The sleeve device deployment system may further comprise one or more intragastric balloons that are configured to be inflatable within a stomach of the mammal. At least a portion of an outer surface of the over-tube may be adapted to reduce friction between the over-tube and the sleeve device.

Particular embodiments of the subject matter described in this document can be implemented to realize one or more of the following advantages. In some embodiments, the devices and methods provided herein can cause weight loss and improvement in diabetes by, among other potential mechanisms, reducing the caloric intake and absorption of an individual. The methods for implanting the devices can be performed endoscopically, thus avoiding the need for the more invasive open or laparoscopic surgical procedures. The endoscopic technique for implanting the devices can provide total direct visualization of the GI tract anatomy in which the devices are implanted and can bypass longer segments of the gastrointestinal tract given utilization of deep enteroscopy techniques and distal release of the device. In some embodiments, each of the proximal and distal ends of the device are anchored in relation to the GI tract to definitively position the device and to provide effective migration resistance. In some embodiments, such anchoring of each of the proximal and distal ends of the device is performed during deployment either sequentially or substantially simultaneously to further enhance the definitive positioning of the device.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices and methods for the medical treatment of conditions such as obesity and various metabolic diseases. For example, this document provides devices and methods for bypassing portions of the GI tract that can reduce nutritional uptake, decrease weight, and improve diabetes control. The devices are fully endoscopically deployable, using substantially complete direct visualization. Some embodiments of the devices are able to bypass the stomach and small intestines and are thus able to recapitulate the physiology of RYGB. The devices and methods provided herein allow the bypass of different lengths of the small intestines and/or the stomach using a distally deployed, fully endoscopic sleeve device delivery technique that utilizes single or double balloon enteroscopy, or regular enteroscopy with a colonoscope. The delivery system provided herein facilitates the deployment of intestinal bypass sleeve devices of various lengths (short and long), and/or combined small intestinal and gastric bypass sleeves with or without intragastric restrictive balloons. The various sleeve lengths and/or ability to bypass the stomach allows for a sequential treatment technique for induction and maintenance of weight loss. This can balance effective weight loss and diabetes resolution with risks of malnutrition and micronutrient deficiency.

The deployment systems and methods provided herein can deliver and anchor different lengths of sleeves and or intragastric balloons using an over-tube that is compatible with single or double balloon enteroscopes or colonoscopes. This deployment system platform will allow deep small bowel insertion under endoscopic guidance with distal-to-proximal sleeve release, thus making endoscopic bypass of the stomach and placement of restrictive gastric balloons feasible, and thus closely replicating the anatomy and physiology of surgical RYGB. In at least some cases, the sleeve devices provided herein can be readily placed and removed endoscopically with procedural sedation or monitored anesthesia moderate sedation only, and on an out-patient basis. Accordingly, the devices and methods provided herein are potentially widely applicable to a large segment of the obese population with mild, moderate, and severe forms of obesity while exhibiting many advantages over bariatric surgery.

Figure 1:
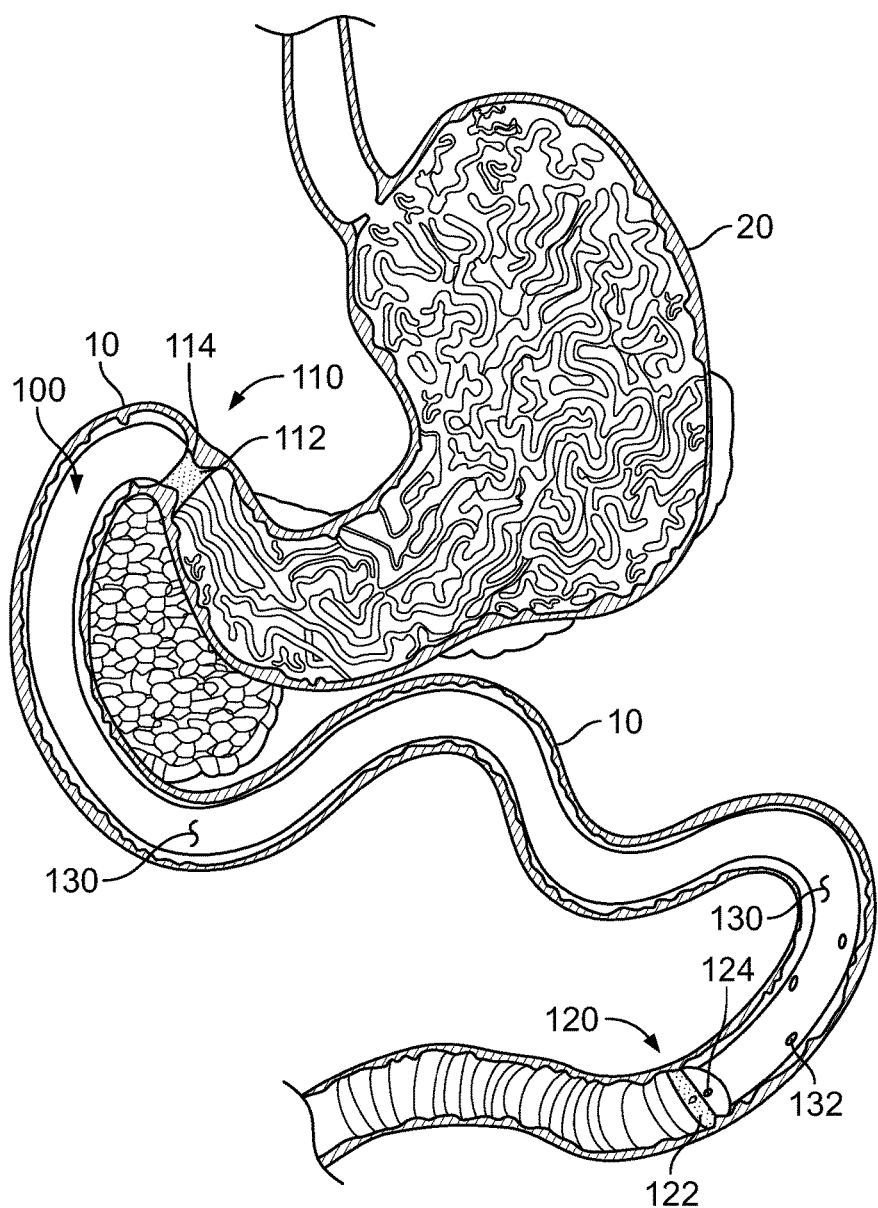
FIG. 1 illustrates an example intestinal bypass sleeve device installed in a GI tract shown in a coronal plane cross-sectional view.

In reference to FIG. 1, an example intestinal bypass sleeve device 100 can be installed in a portion of a small intestine 10 to reduce the nutritional uptake from food and liquids that pass through sleeve device 100. In other words, sleeve device 100 at least partially blocks food and liquids from contacting the portion of small intestine 10 in which sleeve device 100 resides and prevents mixing of food with digestive pancreas and biliary secretions until later in the gastrointestinal tract Consequently, the nutritional uptake from food and liquids can be reduced by the presence of sleeve device 100 and only partially digested nutrients delivered to the distal gastrointestinal tract.

In the depicted implementation, a proximal end 110 of sleeve device 100 is positioned in the patient's pyloric region at the junction between small intestine 10 and stomach 20. However, in other implementations proximal end 110 can be located at other locations within small intestine 10 or stomach 20.

Sleeve device 100 includes proximal end 110, a distal end 120, and a tube 130. Tube 130 extends between proximal end 110 and distal end 120 and is attached to each of proximal end 110 and distal end 120.

Tube 130 can be constructed from a biocompatible flexible polymer such as, but not limited to, silicone, ePTFE, and the like, and combinations of such materials. In some embodiments, tube 130 is constructed with a wall that is thin and flexible so that peristalsis can occur from forces delivered by small intestine 10 through tube 130. In some embodiments, the diameter of tube 130 is slightly less than the inner diameter of small intestine 10 and is consistent along its entire length. However, in some embodiments the diameter of tube 130 may vary along its length.

In some embodiments, tube 130 is impermeable to body fluids and ingested food/liquids. However, in some embodiments, some or all of tube 130 can be porous or semipermeable. In some embodiments, tube 130 includes coatings on at least portions of its interior and/or exterior walls. For example, in some such embodiments the coatings can be included to increase the chemical resistance of tube 130, or to resist infection and/or reduce the potential for tissue inflammatory response. Further, in some embodiments at least portions of the interior and/or exterior of tube 130 are coated with a lubricious coating to reduce friction related to food passing though tube 130.

In some embodiments, tube 130 includes one or more holes 132 (openings through the wall of tube 130) in some locations, such as the distal portion of tube 130. Such holes 132 can advantageously allow pancreaticobiliary secretions to enter tube 130 and to mix with food contents therein for partial digestion.

Sleeve device 100 also includes proximal end 110 and distal end 120. In some embodiments, proximal end 110 and distal end 120 each include stent devices 112 and 122 respectively. Tube 130 can be attached to stent devices 112 and 122 using various techniques such as, but not limited to, crimping, clamping, suturing, heat staking, using adhesives, and the like.

In some embodiments, stent devices 112 and 122 can be self-expanding stents made from materials such as, but not limited to, nitinol, stainless steel, and the like, and combinations of such materials. In the depicted embodiment, stent devices 112 and 122 are frustoconical in shape (flared). As such, migration resistance of stent devices 112 and 122 can be enhanced in some implementations. In some embodiments, one or both of stent devices 112 and 122 are shaped differently, such as, but not limited to, cylindrically, toroidally, and the like.

In some embodiments, one or both of stent devices 112 and 122 can include supplemental anchor features 114 and 124 respectively. In some embodiments, anchor features 114 and 124 can be items such as, but not limited to, barbs, hooks, needles, atraumatic protrusions, and the like, and combinations thereof. Optionally, to increase anti-migration resistance of sleeve device 100, one or both stent devices 112 and 122 can be secured to surrounding tissue by one or more endoscopically installed sutures. In one such example, stent device 112 at proximal end 110 can have about three or four sutures installed to secure stent device 112 in the pyloric region.

In some embodiments, one or both of stent devices 112 and 122 can include one or more radiopaque markers to assist a clinician to fluoroscopically visualize sleeve device 100 during the deployment process. Such radiopaque markers can be comprised of materials such as, but not limited to, platinum, tungsten, tantalum, palladium alloys, and the like, and combinations thereof.

Figure 2:
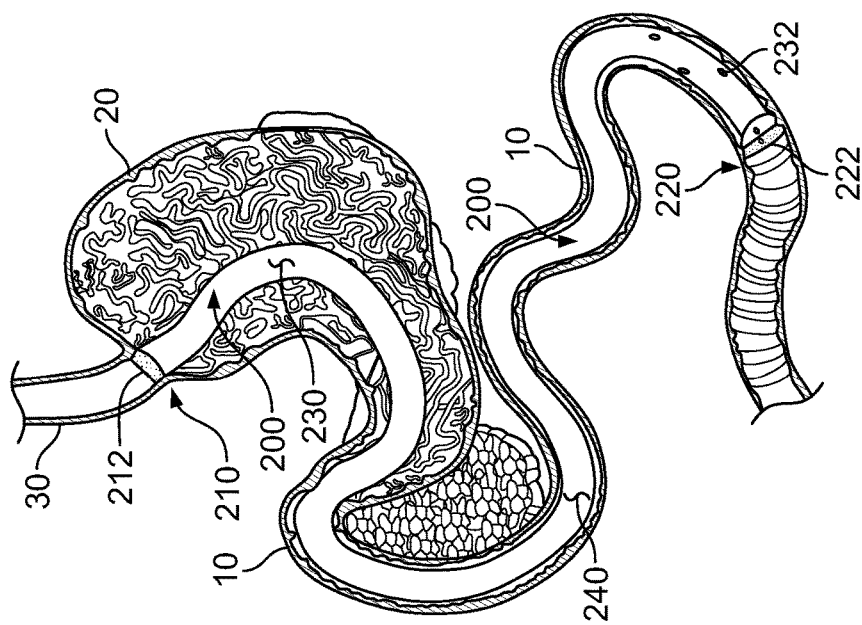
FIG. 2 illustrates an example GI bypass sleeve device installed in a GI tract shown in a coronal plane cross-sectional view.

In reference to FIG. 2, an example GI bypass sleeve device 200 can be installed in a portion of small intestine 10 and in stomach 20 to reduce the nutritional uptake from food and liquids that pass through sleeve device 200. In other words, sleeve device 200 at least partially blocks food and liquids from contacting the portion of small intestine 10 and stomach 20 in which sleeve device 200 resides. Consequently, the nutritional uptake from food and liquids is reduced by the presence of sleeve device 200.

In the depicted implementation, a proximal end 210 of sleeve device 200 is positioned near the esophageal sphincter at the junction of esophagus 30 and stomach 20. However, in other implementations proximal end 210 can be located at other locations within small intestine 10, stomach 20, or esophagus 30.

Sleeve device 200 includes proximal end 210, a distal end 220, a first tube portion 230, and a second tube portion 240. Tube portions 230 and 240 extend between proximal end 210 and distal end 220 and are attached at each of proximal end 210 and distal end 220. In general, first tube portion 230 extends from proximal end 210 to the pyloric region, and second tube portion 240 extends from the distal end of first tube portion 230 in the pyloric region to distal end 220.

Tube portions 230 and 240 can be constructed from a biocompatible flexible polymer as described above in reference to tube 130. In some embodiments, tube portions 230 and 240 are constructed uniformly in relation to each other. However, in some embodiments tube portions 230 and 240 are constructed dissimilarly. For example, in some embodiments first tube portion 230 may be constructed to be more rigid than second tube portion 240. In some such examples, first tube portion 230 may have a wall that is thicker than second tube portion 240, or may be made of a material that is less flexible than second tube portion 240.

Sleeve device 200 also includes proximal end 210 and distal end 220. In some embodiments, proximal end 210 and distal end 220 each include stent devices 212 and 222 respectively. First tube portion 230 can be attached to stent device 212 and second tube portion 240 can be attached to stent device 222 using various techniques such as, but not limited to, crimping, clamping, suturing, using adhesives, and the like.

In some embodiments, stent devices 212 and 222 can be self-expanding stents made from materials such as, but not limited to, nitinol, stainless steel, and the like, and combinations of such materials. In the depicted embodiment, stent devices 212 and 222 are frustoconical in shape (flared). As such, migration resistance of stent devices 212 and 222 can be enhanced in some implementations. In some embodiments, one or both of stent devices 212 and 222 are shaped differently, such as, but not limited to, cylindrically, toroidally, and the like.

In some embodiments, one or both of stent devices 212 and 222 can include supplemental anchor features as described above in regard to anchor features 114 and 124 respectively. Optionally, to increase anti-migration resistance of sleeve device 200, one or both stent devices 212 and 222 can be secured to surrounding tissue by one or more endoscopically installed sutures. In one such example, stent device 212 at proximal end 210 can have about three or four sutures installed to secure stent device 212 near the esophageal sphincter. In some embodiments, one or both of stent devices 212 and 222 can include one or more radiopaque markers as described above in regard to stent devices 112 and 122.

Figure 3:
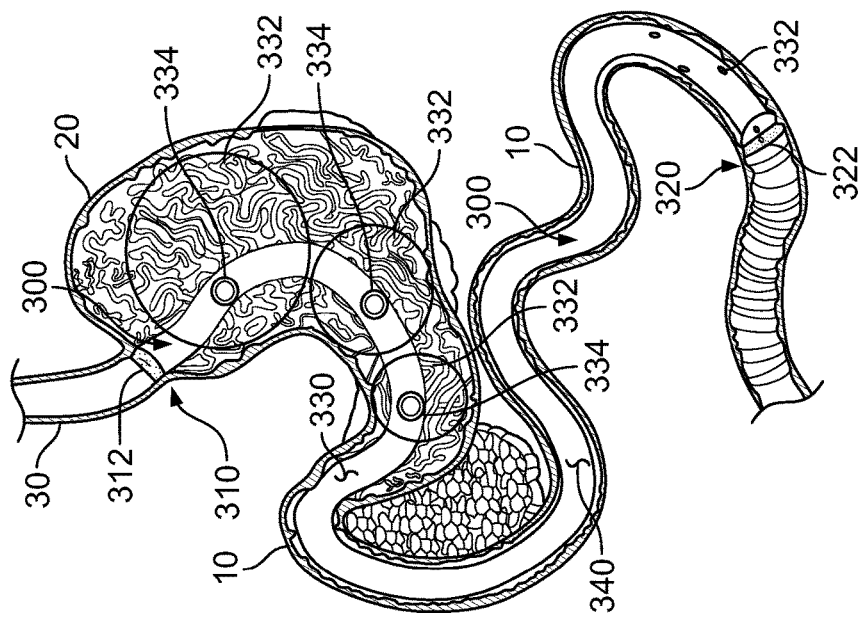
FIG. 3 illustrates another example GI bypass sleeve device installed in a GI tract shown in a coronal plane cross-sectional view.

In reference to FIG. 3, another example GI bypass sleeve device 300 can be installed in a portion of small intestine 10 and in stomach 20 to reduce the nutritional uptake from food and liquids that pass through sleeve device 300. In other words, sleeve device 300 at least partially blocks food and liquids from contacting the portion of small intestine 10 and stomach 20 in which sleeve device 300 resides. Consequently, the nutritional uptake from food and liquids is reduced by the presence of sleeve device 300.

In the depicted implementation, a proximal end 310 of sleeve device 300 is positioned near the esophageal sphincter at the junction of esophagus 30 and stomach 20. However, in other implementations proximal end 310 can be located at other locations within small intestine 10, stomach 20, or esophagus 30.

Sleeve device 300 includes proximal end 310, a distal end 320, a first tube portion 330, and a second tube portion 340.

Tube portions 330 and 340 extend between proximal end 310 and distal end 320 and are attached at each of proximal end 310 and distal end 320. In general, first tube portion 330 extends from proximal end 310 to the pyloric region, and second tube portion 340 extends from the distal end of first tube portion 330 in the pyloric region to distal end 320.

In some embodiments, GI bypass sleeve device 300 is analogous to sleeve device 200 but with the addition of one or more intragastric balloons 332 that are coupled with first tube portion 330. For example, in the depicted embodiment three intragastric balloons 332 are included. The one or more intragastric balloons 332 can be of differing sizes in some embodiments. For example, in the depicted embodiment intragastric balloons 332 are of three different sizes (small in the gastric antrum, medium in the gastric body, and large in the gastric fudus). Other configurations are also envisioned. The one or more intragastric balloons 332 will serve at least three purposes: (1) to support the weight of the food bolus in first tube portion 330 without exerting excessive stress on stent device 312; (2) to be an anti-migration mechanism; and (3) to provide gastric restriction for effective weight loss.

In some embodiments, each of the one or more intragastric balloons 332 includes an inflation port 334. Inflation port 334 can be a septum, a one-way valve, and the like, and combinations thereof. An endoscopic needle can be used to inflate the one or more intragastric balloons 332 via the inflation ports 334 in situ. For example, after deployment of the sleeve device 330 (as described further below) a diagnostic gastroscope can be re-introduced in the inner lumen of first tube portion 330. In some embodiments, inflation ports 334 are visually marked using colors or labels, for example, so that inflation ports 334 can be readily identified endoscopically. Radiopaque markers can also be included in some embodiments. A 25 gauge needle, for example, can then be used to pass through the inflation ports 334 (one at a time). An inflation medium, such as air for example, can then be injected into intragastric balloons 332. This configuration also allows for endoscopic adjustment of the volumes of intragastric balloons 332 during the course of treatment. For example, the volumes of intragastric balloons 332 can be tailored with respect to patient satiety levels and weight loss during the course of treatment.

Tube portions 330 and 340 can be constructed from a biocompatible flexible polymer as described above in reference to tube 130. In some embodiments, tube portions 330 and 340 are constructed uniformly in relation to each other. However, in some embodiments tube portions 330 and 340 are constructed dissimilarly. For example, in some embodiments first tube portion 330 may be constructed to be more rigid than second tube portion 340. In some such examples, first tube portion 330 may have a wall that is thicker than second tube portion 340, or may be made of a material that is less flexible than second tube portion 340.

Sleeve device 300 also includes proximal end 310 and distal end 320. In some embodiments, proximal end 310 and distal end 320 each include stent devices 312 and 322 respectively. First tube portion 330 can be attached to stent device 312 and second tube portion 340 can be attached to stent device 322 using various techniques such as, but not limited to, crimping, clamping, suturing, heat staking, using adhesives, and the like.

In some embodiments, stent devices 312 and 322 can be self-expanding stents made from materials such as, but not limited to, nitinol, stainless steel, and the like, and combinations of such materials. In the depicted embodiment, stent devices 312 and 322 are frustoconical in shape (flared). As such, migration resistance of stent devices 312 and 322 can be enhanced in some implementations. In some embodiments, one or both of stent devices 312 and 322 are shaped differently, such as, but not limited to, cylindrically, toroidally, and the like.

In some embodiments, one or both of stent devices 312 and 322 can include supplemental anchor features as described above in regard to anchor features 114 and 124 respectively. Optionally, to increase anti-migration resistance of sleeve device 300, one or both stent devices 312 and 322 can be secured to surrounding tissue by one or more endoscopically installed sutures. In one such example, stent device 312 at proximal end 310 can have about three or four sutures installed to secure stent device 312 near the esophageal sphincter. In some embodiments, one or both of stent devices 312 and 322 can include one or more radiopaque markers as described above in regard to stent devices 112 and 122.

In reference to FIGS. 4A-4D, in some implementations the GI/intestinal bypass sleeve devices provided herein can be implanted endoscopically using deployment system 400, for example. In the depicted example, intestinal bypass sleeve device 100 is the device illustrated as being endoscopically implanted by deployment system 400. However, the same general techniques that are used to endoscopically implant intestinal bypass sleeve device 100 can also be used to implant any of the other GI/intestinal bypass sleeve devices provided herein.

Figure 4A:
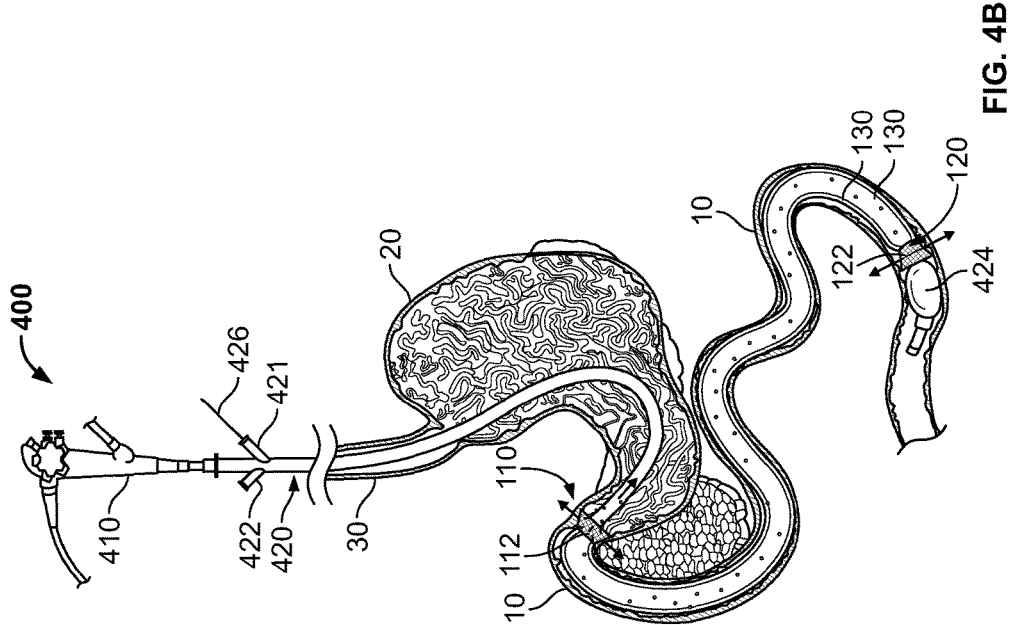
FIGS. 4A-4D are a series of illustrations depicting an example deployment method that can be used to implant the bypass sleeve devices provided herein.

Deployment system 400 includes a scope device 410 and an over-tube 420. Over-tube 420 includes a lumen in which scope device 410 is slidably disposed. Intestinal bypass sleeve device 100 is releasably coupled on the outer surface of a portion of over-tube 420. For example, in some embodiments at least stent devices 112 and 122 are releasably coupled by a friction fit to the outer diameter of a portion of over-tube 420 (when the stent devices 112 and 122 are in a diametrically constrained delivery configuration as shown in FIG. 4A).

In some embodiments, a distal end portion 412 of scope device 410 can extend near to or protrude beyond a distal tip 425 of over-tube 420. As such, while deployment system 400 is advanced into the patient (e.g., through the esophagus 30, stomach 20, and a portion of small intestine 10) to arrive at the configuration shown or at one that is similar to what is shown, the clinician operator can directly visualize the patient's relevant anatomical features that will be affected by sleeve device 100.

In some embodiments, at least distal end portion 412 is steerable by a clinician operator of deployment system 400. As such, when deployment system 400 is being advanced into the patient (e.g., through the esophagus 30, stomach 20, and a portion of small intestine 10) to arrive at the configuration shown or at one that is similar to what is shown, the clinician operator can actively steer/drive the distal end portion 412 of scope device 410. Also during advancement of the deployment system 400, by extension, the clinician can drive/steer distal tip 425 of over-tube 420 as well as distal end 120 of sleeve device 100 (which is releasably coupled to over-tube 420). To reiterate, distal end 120 of sleeve device 100 can be steered/driven to a target anatomical location in small intestine 10 under complete direct visualization by a clinician operator using deployment system 400.

In some embodiments, one or more radiopaque markers may be included at one or more locations on sleeve device 100. For example, the depicted embodiment of sleeve device 100 includes radiopaque markers 116 on proximal stent device 112. In this example, radiopaque markers 116 can be used to assist with fluoroscopic visualization of the location of proximal end 110 so that stent device 112 can be deployed (expanded) in a target location.

Over-tube 420 includes one or more balloon members 424 adjacent to distal tip 425 of over-tube 420. Similar to single or double balloon enteroscopy, this balloon can retract (accordion) the small bowel to allow deeper delivery of longer sleeves if desired. Furthermore, upon arrival of distal end portion 412 of scope device 410 in a target location within small intestine 10, one or more balloon member 424 can be inflated to temporarily anchor the distal portion of deployment system 400 within small intestine 10. Such is the configuration shown in FIG. 4A.

Figure 4B:
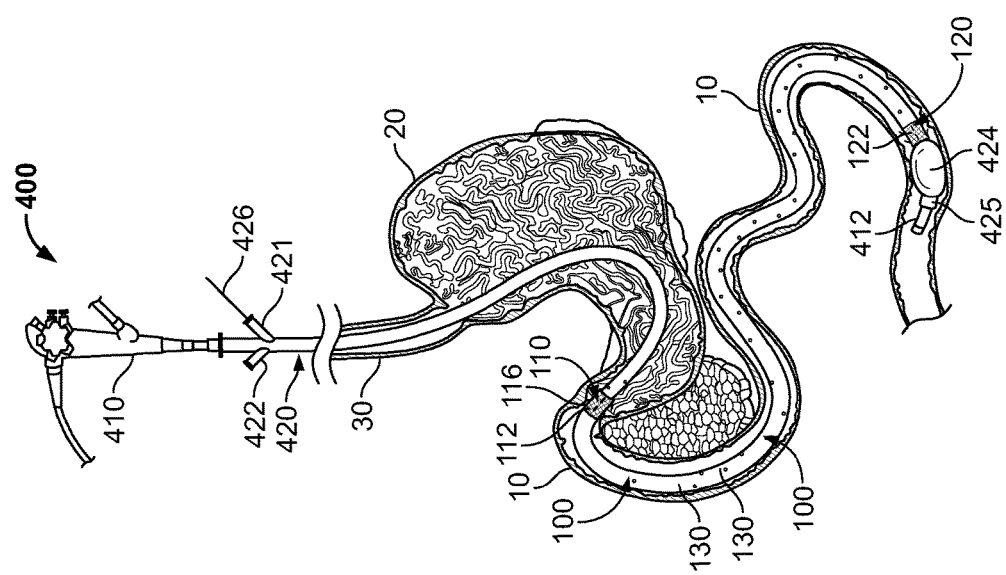

Referring now to FIG. 4B in particular, stent devices 112 and 122 can be deployed (expanded) by a clinician operator when sleeve device 100 is located within the patient's anatomy at a desired location and in a desired configuration. As described previously, stent devices 112 and 122 are initially constrained in a low-profile delivery configuration on the over-tube 420 when the deployment system 400 is driven into the desired location. Thereafter, in some embodiments an actuator 426 (e.g., a wire) can be manipulated to release stent devices 112 and 122 from being constrained. Upon release of their constraints, stent devices 112 and 122 can self-expand to conform to the surrounding tissue, and to thereby anchor the proximal end 110 and distal end 120 of sleeve device 100 in relation to the GI/intestinal anatomy of the patient. In addition, expansion of stent devices 112 and 122 decouples sleeve device 100 from over-tube 420. However, at this stage over-tube 420 remains within sleeve device 100 as shown.

In the depicted embodiment, the actuator 426 is a wire that runs the length of over-tube 420 and exits from a port 421 of over-tube 420. Pulling wire 426 releases the diametrical constraints on stent devices 112 and 122. In some embodiments, delivery system 400 is configured such that stent devices 112 and 122 have individual actuators 426 whereby stent devices 112 and 122 can be deployed individually. In some embodiments, delivery system 400 is configured such that stent devices 112 and 122 have a common actuator 426 whereby stent devices 112 and 122 can be deployed either simultaneously or sequentially by manipulation of the common actuator 426.

Figure 4D:
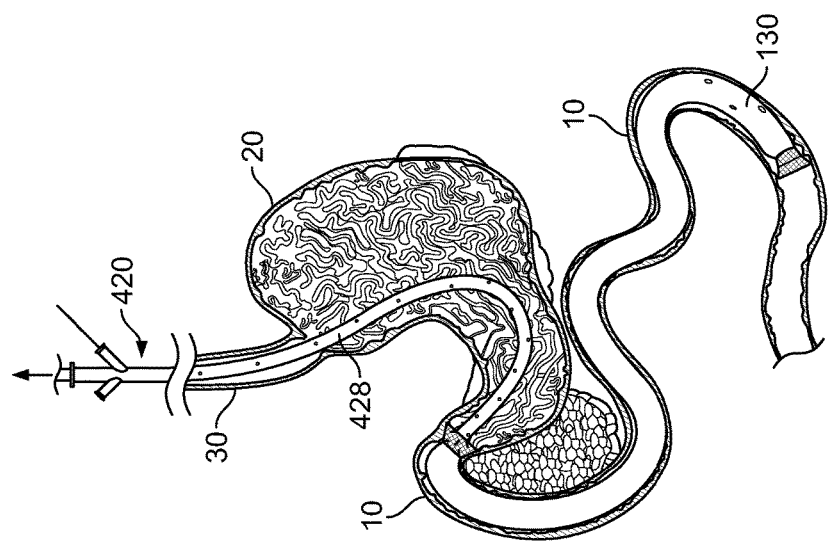
Figure 4C:
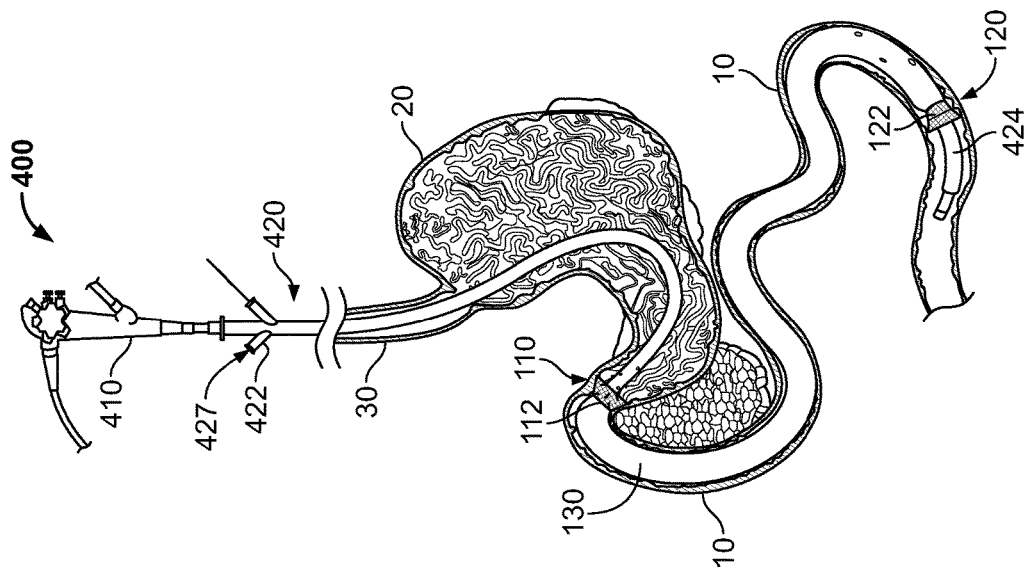

Referring now to FIGS. 4C and 4D in particular, the removal of deployment system 400 is depicted. Such removal steps can include, for example: (i) deflation of balloon member 424, (ii) injection of a fluidic lubricant 427 into port 422 of over-tube 420, (iii) withdrawal of scope device 410 from within over-tube 420, and (iv) withdrawal of over-tube 420 from within sleeve device 100. It is not necessarily required in all implementations to perform those removal steps in the order listed. Nor is each of those removal steps necessarily required in all implementations.

The injection of fluidic lubricant 427 into port 422 of over-tube 420 assists the process of deploying sleeve 100 by, for example: (i) diametrically expanding tube 130 of sleeve 100 and (ii) reducing friction between the outer surface of over-tube 420 and inner surface of tube 130. In some implementations, fluids such as, but not limited to, water, saline, and the like can be used as fluidic lubricant 427. Fluid lubricant 427 can be injected into a port 422 of over-tube 420. From port 422, one or more lumens in over-tube 420 can convey fluid lubricant 427 distally within over-tube 420. The outer surface of over-tube 420 can include one or more openings 428 through which fluid lubricant 427 can flow so as to exit over-tube 420 and enter into the space between over-tube 420 and sleeve device 100.

In some embodiments, at least some portions of the surface of over-tube 420 are treated to reduce friction between over-tube 420 and sleeve device 100. For example, in some such embodiments a hydrophilic coating; such as having four thin hydrophilic coated lines spanning the outer surface of the overtube (one on each outer quadrant), can be disposed on at least some portions of the outer surface of over-tube 420. Such a feature, along with fluid lubricant 427, can facilitate a substantially frictionless withdrawal of over-tube 420 from sleeve device 100 without materially affecting the deployed configuration and location of sleeve device 100 within the patient.

The GI/intestinal bypass sleeve devices provided herein are readily removable endoscopically. For the small intestinal only sleeve (e.g., sleeve device 100) a long wire on the distal stent is grasped by an endoscopic forceps (from within the tube of the sleeve device) and pulled into the endoscope working channel. This will at least partially diametrically collapse the distal stent. The small intestinal sleeve is then inverted into the stomach by withdrawal of the endoscope and wire. Once in the stomach, the tube is cut in the middle by a cutting snare or endoscopic scissors. The distal stent wire (which is everted into the stomach) is grasped again by an endoscopic forceps and pulled into the working channel of the endoscope to constrain and pull the cut half of the tube/sleeve. Once this half is pulled the scope is re-introduced in the stomach and the wire of the proximal stent is grasped and pulled into the working channel of a gastroscope to constrain and remove the second cut half of the tube/sleeve.

Removal of GI bypass sleeve devices (e.g., sleeve device 200 or sleeve device 300) can be performed as follows. The gastric balloons (if present) are deflated endoscopically by an endoscopic needle as described above. The distal stent wire is grasped and constrained by a forceps into the working channel of the endoscope and the small intestinal tube is inverted into the gastric tube. The proximal stent wire is grasped and constrained by a forceps into the working channel of the endoscope and then the entire sleeve device is pulled out of the patient's mouth. The use of an esophageal length over-tube for removal of the GI sleeve device is optional.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for reducing weight and caloric uptake of a mammal, wherein said method comprises:
    inserting a sleeve device deployment system into a GI tract of the mammal, wherein the sleeve device deployment system comprises:
        an endoscope;
        an over-tube including a lumen in which at least a portion of the endoscope is disposed; and
        a sleeve device comprising:
            a proximal stent;
            a distal stent; and
            a tube extending between the proximal stent and the distal stent and attached to each of the proximal and distal stents,
        wherein the tube and each of the proximal and distal stents are disposed on the over-tube, and wherein each of the proximal and distal stents are configured in a low profile delivery configuration during the inserting;
    visualizing, using the endoscope, a portion of the GI tract in which the sleeve device will be deployed, including visualizing the portion of the GI tract in which the distal stent will be deployed;
    deploying the sleeve device such that each of the proximal and distal stents are reconfigured to have a diametrical profile that is larger than the low profile delivery configuration of each of the proximal and distal stents, and such that each of the proximal and distal stents make contact with surrounding tissue of the GI tract so as to fixate each of the proximal and distal stents in relation to the surrounding tissue of the GI tract; and
    withdrawing the endoscope and the over-tube while leaving the sleeve device within the GI tract.

2. The method of claim 1, wherein the mammal is a human.

3. The method of claim 1, further comprising, prior to the withdrawing, injecting a fluid into a space between the over-tube and the sleeve device.

4. The method of claim 1, wherein the deploying further comprises reconfiguration of the distal stent to have the diametrical profile that is larger than the low profile delivery configuration prior to reconfiguration of the proximal stent to have the diametrical profile that is larger than the low profile delivery configuration.

5. The method of claim 1, wherein the sleeve device deployment system is steerable, and wherein the inserting includes steering the sleeve device deployment system within the GI tract.

6. The method of claim 1, wherein the proximal stent is deployed so as to make contact with surrounding tissue of the GI tract in a pyloric region of the GI tract.

7. The method of claim 1, wherein the proximal stent is deployed so as to make contact with surrounding tissue of the GI tract near an esophageal sphincter of the GI tract.

8. The method of claim 1, wherein the sleeve device further comprises one or more radiopaque markers, and wherein fluoroscopy is used to visualize a location of at least a portion of the sleeve device prior to the deploying.

9. A sleeve device deployment system configured to deploy a sleeve device into a GI tract of a mammal, wherein the sleeve device deployment system comprises:
    an over-tube defining a lumen configured for receiving at least a portion of an endoscope; and
    a sleeve device comprising:
        a proximal stent;
        a distal stent; and
        a tube extending between the proximal stent and the distal stent and attached to each of the proximal and distal stents,
    wherein the tube and each of the proximal and distal stents are configured to be disposed on the over-tube for deployment of the sleeve device and separated from the over-tube so as to deploy the sleeve device, and wherein each of the proximal and distal stents are configurable in a low profile delivery configuration and a deployed configuration that has a diametrical profile that is larger than the low profile delivery configuration.

10. The sleeve device deployment system of claim 9, wherein the sleeve device deployment system is configured to deploy the sleeve device by reconfiguring the distal stent prior to reconfiguring the proximal stent.

11. The sleeve device deployment system of claim 9, wherein at least a portion of an outer surface of the over-tube is adapted to reduce friction between the over-tube and the sleeve device.

12. The sleeve device deployment system of claim 9, further comprising an endoscope positionable within the lumen.

13. The sleeve device deployment system of claim 9, wherein the proximal stent and the distal stent are comprised of nitinol or stainless steel.

14. The sleeve device deployment system of claim 9, wherein the tube defines one or more openings through a wall of the tube.

15. A sleeve device deployment system configured to deploy a sleeve device into a GI tract of a mammal, wherein the sleeve device deployment system comprises:
    an over-tube defining a lumen configured for receiving at least a portion of an endoscope; and
    a sleeve device comprising:
        a proximal stent;
        a distal stent;
        a tube extending between the proximal stent and the distal stent and attached to each of the proximal and distal stents; and
        one or more intragastric balloons that are configured to be inflatable within a stomach of the mammal,
    wherein the tube and each of the proximal and distal stents are configured to be disposed on the over-tube for deployment of the sleeve device and separated from the over-tube so as to deploy the sleeve device, and wherein each of the proximal and distal stents are configurable in a low profile delivery configuration and a deployed configuration that has a diametrical profile that is larger than the low profile delivery configuration.

* * * * *